United States Patent [19]

van Hes et al.

[11] 4,379,157
[45] Apr. 5, 1983

[54] SULPHONYL COMPOUNDS, METHOD OF PREPARING THE NEW COMPOUNDS, AS WELL AS APHICIDAL COMPOSITIONS ON THE BASIS OF THE NEW COMPOUNDS

[75] Inventors: Roelof van Hes; Arnoldus C. Grosscurt; Wouter Balk, all of Weesp, Netherlands

[73] Assignee: Duphar International Research B.V., Netherlands

[21] Appl. No.: 226,533

[22] Filed: Jan. 19, 1981

[30] Foreign Application Priority Data

Jan. 23, 1980 [NL] Netherlands .......................... 8000414

[51] Int. Cl.³ ........................................... C07D 275/06
[52] U.S. Cl. ..................................... 424/270; 548/207
[58] Field of Search .......................... 548/207; 424/270

[56] References Cited

FOREIGN PATENT DOCUMENTS 48-24735 7/1973 Japan .................................... 424/270

OTHER PUBLICATIONS

Horsfall, James; *Principles of Fungicidal Action,* pp. 72, 73. (1956).
Burger, Alfred; *Medicinal Chemistry,* p. 43 (1960).
Balode, D; *Chemical Abstracts,* vol. 92, No. 180415v.
Bhargava, P. N. et al., *Journal of the Indian Chemical Society,* vol. 56, pp. 377-379.

*Primary Examiner*—Donald G. Daus
*Assistant Examiner*—G. Hendricks
*Attorney, Agent, or Firm*—Stevens, Davis, Miller & Mosher

[57] ABSTRACT

The invention relates to new sulphonyl compounds of the general formula

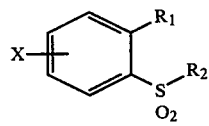

wherein
  X is a halogen atom, a phenoxy group, or an alkyl group or alkoxy group having 1-4 carbon atoms and substituted, if desired, with halogen;
  $R_1$ is a cyano group, and
  $R_2$ is an amino group which, if desired, may be substituted with halogen, with one or two alkenyl groups or alkynyl groups having 2-6 carbon atoms or with one or two alkyl groups having 1-6 carbon atoms, which alkyl groups, together with the nitrogen atom to which they are bound, may form a saturated heterocyclic ring, which ring may also contain a second hetero atom selected from the group consisting of nitrogen, oxygen and sulphur, or which alkyl groups may be substituted with an alkoxy group, having 1-4 carbon atoms, or with a dialkylamino group having 2-6 carbon atoms the alkyl groups of which, together with the nitrogen atom to which they are bound, may form a saturated heterocyclic ring;
or wherein
  $R_1$ and $R_2$ together form a S,S-dialkylsulphoximido group the alkyl groups of which comprise 1-4 carbon atoms, or a 1-amino-2-azavinylene group, of which the amino group is substituted, if desired, with a cycloalkylcarbamoyl group having 4-8 carbon atoms, an alkylcarbamoyl group having 2-5 carbon atoms, a dialkylamino group the alkyl group of which comprise 1-4 carbon atoms, or an alkyl group having 1-4 carbon atoms which alkyl group may be substituted with a hydroxy group or one or more halogen atoms;
or wherein
  $R_1$ and $R_2$ together form a 1-imino-2-azaethylene group of which the ring nitrogen is substituted with an alkyl group or alkenyl group having 1-4 carbon atoms, and of which the imino group may be substituted with a substituted or non-substituted phenylcarbamoyl group, having aphicidal activity. After having been processed to compositions, the compounds may be used for the control of aphids in agriculture, horticulture and forestry in a dosage from 20 to 5,000 g of active substance per hectare.

14 Claims, No Drawings

SULPHONYL COMPOUNDS, METHOD OF PREPARING THE NEW COMPOUNDS, AS WELL AS APHICIDAL COMPOSITIONS ON THE BASIS OF THE NEW COMPOUNDS

The invention relates to new sulphonyl compounds, and to a method of preparing the new compounds. The invention also relates to aphicidal compositions on the basis of the new compounds and to the use of these compositions for the control of aphids in agriculture, horticulture and forestry.

Japanese Patent Application No. 73/24735 discloses benzo[d]isothiazole-1,1-dioxides having fungicidal activity, for example 3-amino-benzo[d]isothiazole-1,1-dioxide.

German Patent Application ("Offenlegungsschrift") No. 1670797 discloses benzoisothiazole-1,1-dioxides, e.g. 3-dimethyl-amino-6-chlorobenzoisothiazole-1,1-dioxide, and a method of preparing the compounds; it is stated that the prepared compounds are intermediates for the preparation of dyes and pesticides. In neither patent application mention is made of an insecticidal or aphicidal activity of the prepared compounds.

It has now been found that new sulphonyl compounds of the general formula

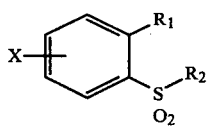

wherein

X is a halogen atom, a phenoxy group, or an alkyl group or alkoxy group having 1–4 carbon atoms and substituted, if desired, with halogen;

$R_1$ is a cyano group, and $R_2$ is an amino group which, if desired, may be substituted with halogen, with one or two alkenyl groups or alkynyl groups having 2–6 carbon atoms or with one or two alkyl groups having 1–6 carbon atoms, which alkyl groups, together with the nitrogen atom to which they are bound, may form a saturated heterocyclic ring, which ring may also contain a second hetero atom selected from the group consisting of nitrogen, oxygen and sulphur, or which alkyl groups may be substituted with an alkoxy group having 1–4 carbon atoms or with a dialkylamino group having 2–6 carbon atoms the alkyl groups of which, together with the nitrogen atom to which they are bound, may form a saturated heterocyclic ring;

or wherein $R_1$ and $R_2$ together form a S,S-dialkylsulphoximido group the alkyl groups of which comprise 1–4 carbon atoms, or a 1-amino-2-azavinylene group, of which the amino group is substituted, if desired, with a cycloalkylcarbamoyl group having 4–8 carbon atoms, an alkylcarbamoyl group having 2–5 carbon atoms, a dialkylamino group the alkyl groups of which comprise 1–4 carbon atoms, or an alkyl group having 1–4 carbon atoms which alkyl group may be substituted with a hydroxy group or one or more halogen atoms;

or wherein $R_1$ and $R_2$ together form a 1-imino-2-azaethylene group of which the ring nitrogen is substituted with an alkyl group or alkenyl group having 1–4 carbon atoms, and of which the imino group may be substituted with a substituted or non-substituted phenylcarbamoyl group, have an aphicidal activity.

The sulphonyl compound known from the above German patent application shows not any aphicidal activity, even at a concentration of 300 ppm. Although the compound known as a fungicide from the above-mentioned Japanese patent application proves to have a slight aphicidal activity, said aphicidal activity is well surpassed by that of chemically related sulphonyl compounds according to the invention, as will become apparent from the results hereinafter. These results have been obtained by testing the compounds on Aphis fabae according to the method described in Example IX.

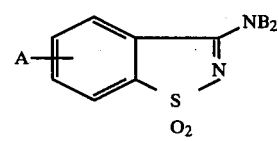

| compound | A | B | \multicolumn{6}{c}{Activity against Aphis fabae Conc. in mg of act. subst. per 1.} |
|---|---|---|---|---|---|---|---|---|
| | | | 300 | 100 | 30 | 10 | 3 | 1 |
| known as intermediate from German pat. appln. 1670797 | 6-Cl | CH₃ | − | | | | | |
| known as fungicide from Jap. pat. appln. 73/24735 | H | H | + | ± | − | | | |
| according to the invention | 4-Cl | H | + | + | + | + | ± | − |

The meaning of the symbols is as follows:
+ = 90–100% mortality
± = 50–90% mortality
− = < 50% mortality.

Of the above-mentioned aphicidal compounds prove to be most active compounds of the general formula

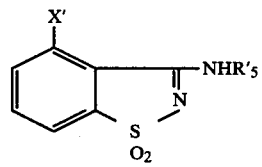

wherein

X' is fluorine atom or a chlorine atom, and

R'₅ is a hydrogen atom, a 2-chloroethyl group, or a cyclohexylcarbamoyl group, and also compounds of the general formula

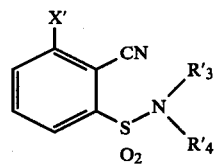

wherein

X' has the above meaning, and

R'₃ and R'₄ are equal or different and represent hydrogen atoms or alkyl groups having 1–4 carbon atoms, and also compounds of the general formula

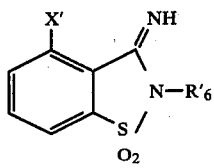

wherein
X' has the above meaning, and
R'$_6$ is a methyl group or ethyl group.

Examples of very suitable aphicidal compounds are:
(1) 3-amino-4-chlorobenzo[d]isothiazole-1,1-dioxide,
(2) 3-(3-cyclohexylureido)-4-chlorobenzo[d]isothiazole-1,1-dioxide,
(3) 3-amino-4-fluorobenzo[d]isothiazole-1,1-dioxide,
(4) 3-(2-chloroethyl)amino-4-chlorobenzo[d]isothiazole-1,1-dioxide,
(5) 2-cyano-3-chlorobenzenesulphonamide,
(6) 2-cyano-3-chloro-N-isopropylbenzenesulphonamide,
(7) 2-cyano-3-fluoro-N,N-diethylbenzenesulphonamide,
(8) 2-cyano-3-fluoro-N-isopropylbenzenesulphonamide,
(9) 2-cyano-3-fluorobenzenesulphonamide,
(10) 2-cyano-3-fluoro-N,N-dimethylbenzenesulphonamide,
(11) 2-methyl-3-imino-4-chlorobenzo[d]isothiazoline-1,1-dioxide,
(12) 2-methyl-3-imino-4-fluorobenzo[d]isothiazoline-1,1-dioxide, and
(13) 2-ethyl-3-imino-4-fluorobenzo[d]isothiazoline-1,1-dioxide. Of the above compounds appeared to be excellently effective compound no. (1).

Examples of other new sulphonyl compounds having aphicidal activity according to the invention are:
(14) 3-(3-methylureido)-4-chlorobenzo[d]isothiazole-1,1-dioxide,
(15) 3-n-butylamino-4-chlorobenzo[d]isothiazole-1,1-dioxide,
(16) 2-cyano-3-chloro-N,N-diallylbenzenesulphonamide,
(17) 2-cyano-3-fluoro-N,N-diallylbenzenesulphonamide,
(18) 2-cyano-3-fluoro-N-(3-methyl-1-butyn-3-yl)benzenesulphonamide,
(19) 1-(2-cyano-3-fluorophenyl)sulphonylpiperidine,
(20) 1-(2-cyano-3-fluorophenyl)sulphonylmorpholine,
(21) 2-cyano-3-methyl-N,N-dimethylbenzenesulphonamide,
(22) 2-cyano-3-methyl-N,N-diallylbenzenesulphonamide,
(23) 2-allyl-3-imino-4-chlorobenzo[d]isothiazoline-1,1-dioxide,
(24) 2-methyl-3-N-(4-ethoxyphenylcarbamoyl)imino-4-chlorobenzo[d]isothiazoline-1,1-dioxide,
(25) 2-cyano-3-fluoro-N,N-dichlorobenzenesulphonamide,
(26) S,S-dimethyl-N-(2-cyano-3-fluorophenylsulphonyl)sulphoximide,
(27) 1-(2-cyano-3-fluorophenyl)sulphonylpyrrolidine,
(28) 2-cyano-5-trifluoromethoxy-N,N-dimethylbenzenesulphonamide,
(29) 2-cyano-5-chloro-N,N-dimethylbenzenesulphonamide,
(30) 2-cyano-3-chloro-N-(2-methoxyethyl)benzenesulphonamide,
(31) 3-(1-hydroxybutyl-2)amino-4-chlorobenzo[d]isothiazole-1,1-dioxide,
(32) 3-amino-4-methylbenzo[d]isothiazole-1,1-dioxide,
(33) 3-amino-4-methoxybenzo[d]isothiazole-1,1-dioxide,
(34) 3-N',N'-dimethylhydrazino-4-chlorobenzo[d]isothiazole-1,1-dioxide,
(35) 3-amino-4-phenoxybenzo[d]isothiazole-1,1-dioxide,
(36) 2-allyl-3-imino-4-fluorobenzo[d]isothiazoline-1,1-dioxide, and
(37) 2-methyl-3-imino-4-methoxybenzo[d]isothiazoline-1,1-dioxide.

The substances according to the invention may be used for the control of aphids in agriculture, horticulture and forestry.

For practical application the substances according to the invention are usually processed to compositions. In such compositions the active substance is mixed with solid carrier material or is dissolved or dispersed in liquid carrier material, if desired in combination with auxiliary substances such as emulsifiers, wetting agents, dispersing agents and stabilizers.

Examples of compositions according to the invention are aqueous solutions and dispersions, oily dispersions, solutions in organic solvents, pastes, dusting powders, dispersing powders, miscible oils, granules, pellets, invert emulsions, aerosol compositions and fumigating candles.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marlow), organic granules (for example, dried coffee grounds, cut tobacco stems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attaclay, colloidal SiO₂ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution; these miscible oils are also called emulsifyable concentrates. Suitable solvents are, for example, xylene, toluene, petroleum distillates which are rich in aromates, for example, solvent naphtha, distilled tar oil and mixtures of these liquids. As emulsifiers may be used, for example, polyoxyethyelene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent and, if desired, a surface-active substance has been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

Insecticides, for example 1. organic chlorine compounds, for example 6,7,8,9,10,10-hexachloro-1,5,5a,6,9,9a-hexahydro-6,9-methano-2,4,3-benzo[e]-dioxathiepine-3-oxide;
2. carbamates, for example: 2-dimethylamino-5,6-dimethylpyrimidin-4-yl dimethyl carbamate and 2-isopropoxyphenyl methyl-carbamate;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1(2,4,5-trichlorophenyl)vinyl di(m)ethyl phosphate;
4. O,O-di(m)ethyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-6-methylpyrimidin-4-yl-, and O-4-nitrophenyl O,O-di(m)ethyl phosphorothioate;
5. O,O-di(m)ethyl phosphorodithioates, for example, S-methylcarbamoylmethyl-, S-2-ethylthioethyl-, S-(3,4-dihydro-4-oxobenzo[d]-1,2,3-triazin-3-ylmethyl-, S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethyl phosphorodithioate;
6. phosphonates, for example, dimethyl 2,2,2-trichloro-1-hydroxyethylphosphonate;
7. benzoylurea, for example, N-(2,6-difluorobenzoyl)-N'-(4-chlorophenyl)urea;
8. natural and synthetic pyrethroids;
9. amidines, for example, N'-(2-methyl-4-chlorophenyl)-N,N-dimethylformamidine; and
10. microbial insecticides, such as Bacillus thuringiensis.

Acaricides, for example 1. organic tin compounds, for example, tricyclohexyl tin hydroxide and di[tri-(2-methyl-2-phenylpropyl)tin]oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;
and furthermore: 3-chloro-α-ethoxyimino-2,6-dimethoxybenzyl benzoate and O,O-dimethyl S-methylcarbamoyl methyl phosphorothioate.

Fungicides, for example 1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate; 3. 1-acyl- or 1-carbamoyl-N-benzimidazole (-2) carbamates and 1,2-bis (3-alkoxycarbonyl-2-thiureido)benzene, and furthermore 2,4-dinitro-6-(2-octylphenylcronotae), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2- butanone, α-(2-chlorophenyl)-α-(4-chlorophenyl)-5-pyrimidinemethanol, 1-(isopropylcarbamoyl)-3-(3,5-dichlorophenyl)hydantoin, N-(1,1,2,2-tetrachloroethylthio)-4-cyclohexene-1,2-carboximide, N-trichloromethylmercapto-4-cyclohexene-1,2-dicarboximide, and N-tridecyl-2,6-dimethylmorpholine.

The dosage of the composition according to the invention desired for practical applications will, of course, depend on various factors, for example, field of application, selected active substance, form of composition, nature and extent of the infection and the weather conditions.

In general it holds that favourable results are obtained with a dosage which corresponds to 20 to 5,000 g of the active substance per hectare, preferably 100 to 500 g per hectare.

As a particular aspect of the invention it was found that the compositions according to the invention have a considerably stronger aphicidal activity when, in addition to the above-mentioned ingredients, they contain one or more of the following substances: an aliphatic or naphtenic mineral oil, a vegetable oil, a glycol ether, an alkylated benzene, a polyoxyethylene compound, urea, a polymeric resin compound, and a surfactant such as a polyoxyethylene sorbitan ester, a fatty acid polyglycol ester, an alkylated phenol polyoxyethylene, a polyoxyethylene alkyl ether or a quaternary ammonium compound.

As examples of additives suitable for this purpose may be mentioned the substances described in Example XIV. The additives to be used may, of course, cause no or at least no noticeable phytotoxicity. A small phytotoxicity of the additive need not be a drawback provided the composition also comprises a small quantity of a phytotoxicity-reducing substance, for example, wool fat, wool fatty alcohol, wool fatty acid or an ester of wool fatty alcohol or wool fatty acid. The quantity of the additive may vary within wide limits dependent on the application, and usually is between 10 and 10,000 ml per hectare.

The compounds according to the invention are new substances which can be prepared in a manner known per se for the synthesis of related compounds.

For example, compounds of the general formula

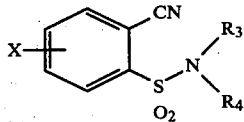

wherein
X has the above meaning, and
$R_3$ and $R_4$ are equal or different and represent hydrogen atoms, halogen atoms, alkenyl groups or alkynyl groups having 2–6 carbon atoms, alkyl groups having 1–6 carbon atoms, which alkyl groups may be substituted with an alkoxy group having 1–4 carbon atoms or with a dialkylamino group having 2–6 carbon atoms the alkyl groups of which, together with the nitrogen atom to which they are bound, may form a saturated heterocyclic ring,
or wherein
$R_3$ and $R_4$ together with the nitrogen atom to which they are bound, form a S,S-dialkylsulphoximido group the alkyl groups of which comprise 1–4 carbon atoms, or a saturated heterocyclic ring, which ring may comprise in addition a second hetero atom selected from the group consisting of nitrogen, oxygen and sulphur,
can be prepared by reacting a compound of the general formula

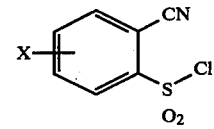

with an amine of the general formula

In this reaction the starting amine is present in an at least bimolar quantity calculated on the acid chloride, so as to bind the HCl formed. The reaction is preferably carried out in a polar organic solvent which is inert with respect to the reaction components, for example an alcohol (for example, ethanol), an ether (for example, diethyl ether), dimethyl formamide, acetonitrile, or water (provided the acid chloride used is sufficiently resistent to hydrolysis under the reaction conditions used), or in a mixture of these solvents. The reaction is carried out at a temperature between 0° C. and the boiling point of the solvent, preferably at a temperature between 0° C. and room temperature. When ammonia or a primary amine is used as an amine, a reaction temperature of approx. 0° C. is desired to reduce the possibility of undesired subsequent reactions.

After the above reaction the compound obtained having the general formula

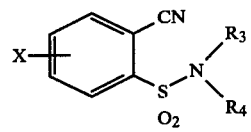

if desired, if $R_3$ and $R_4$ both represent hydrogen atoms, may be reacted with a hypochlorite of hypobromite to produce a compound in which $R_3$ and $R_4$ both are chlorine or bromine atoms, which compound, if desired, after conversion into the N-mono-alkalimetal derivative is reacted with a dialkylsulphoxide, the alkyl groups of which comprise 1–4 carbon atoms, to produce a compound of the last formula, wherein $R_3$ and $R_4$ together with the nitrogen atom to which they are bound form a S,S-dialkylsulphoximido group. The reaction with a hypochlorite or hypobromite, preferably an alkalimetal hypochlorite or hypobromite, e.g. sodium hypochlorite or hypobromite, is carried out in water or in a mixture of water and a water-miscible solvent, at a temperature between 0° C. and 100° C. or the boiling point of the solvent, preferably at room temperature. The conversion into the N-alkalimetal derivative, e.g. the sodium compound, is effected with an aqueous alkalimetalhydroxide solution at a temperature between room temperature and 100° C. The reaction with a dialkylsulphoxide, e.g. dimethylsulphoxide, is carried out at a reaction temperature between room temperature and the boiling point of the solvent. Generally the dialkylsulphoxide used as a reactant, is also used as the solvent. The reaction can be catalyzed by a suitable catalyst, e.g. CuCl₂.

Compounds of the general formula

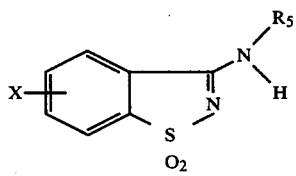

wherein
X has the above meaning, and
R₅ is a hydrogen atom, a cycloalkylcarbamoyl group having 4–8 carbon atoms, an alkylcarbamoyl group having 2–5 carbon atoms, a dialkylamino group the alkyl groups of which comprise 1–4 carbon atoms, or an alkyl group having 1–4 carbon atoms which alkyl group may be substituted with a hydroxy group or one or more halogen atoms, can be prepared in two manners, namely
(a) by reacting a compound of the general formula

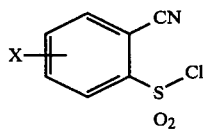

with NH₃, after which the resulting product of the general formula

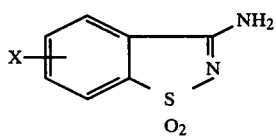

is reacted, if desired, with a cycloalkylisocyanate having 4–8 carbon atoms, an alkylisocyanate having 2–5 carbon atoms, a N,N-dialkylhydrazine the alkyl groups of which comprise 1–4 carbon atoms, or an alkylamine the alkyl group of which has 1–4 carbon atoms and may be substituted with a hydroxy group or one or more halogen atoms, or
(b) by reacting a compound of the general formula

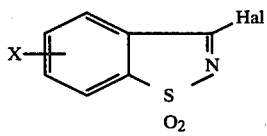

wherein
Hal is a halogen atom, with an amine of the general formula

R₅—NH₂

The reaction with NH₃ mentioned in sub (a) is preferably carried out in a polar organic solvent, for example an ether (for example, diethyl ether or dioxane), an alcohol (for example, ethanol), dimethylformamide, acetonitrile or water, or in a mixture of a polar organic solvent in water, at room temperature or elevated temperature, for example, at the boiling point of the solvent used. The subsequent reaction with an amine or hydrazine described sub (a) is preferably carried out under the same reaction conditions. The subsequent reaction with isocyanate described sub (a) is preferably carried out in a polar organic solvent, for example, acetonitrile or an ether, for example, diethyl ether, in the presence of a strong organic base, for example, triethylamine, at a reaction temperature between 0° C. and the boiling point of the solvent used. The reaction described sub (b) is preferably carried out in a polar organic solvent, for example, acetonitrile, dimethylformamide, an ether (for example, diethyl ether), an alcohol (for example, ether alcohol), or water, or in a mixture of these solvents, at a reaction temperature between 0° C. and room temperature, preferably at approx. 0° C.

Compounds of the general formula

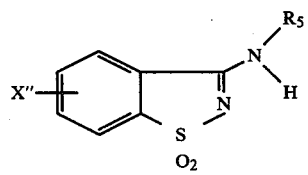

wherein
X" is a phenoxy group or an alkoxy group having 1–4 carbon atoms and substituted, if desired, with halogen, and
wherein
R₅ has the above meaning, may also be prepared by reacting a compound of the general formula

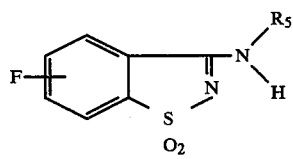

with phenol or an alcohol having 1–4 carbon atoms and substituted if desired, with halogen. This reaction is carried out in the presence of a suitable base, e.g. an alkalimetalphenoxide or -alkoxide, in an inert organic solvent, e.g. an alcohol or acetonitrile, at a reaction temperature between 0° C. and the boiling point of the solvent used, preferably at an elevated temperature.

Compounds of the general formula

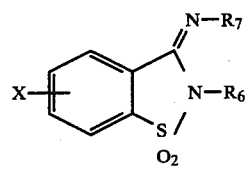

Wherein
X has the above meaning,
R₆ is an alkyl group or an alkenyl group having 1–4 carbon atoms, and
R₇ is a hydrogen atom or a substituted or non-substituted phenylcarbamoyl group,
can be prepared by reacting a compound of the general formula

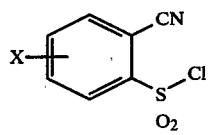

with an amine of the general formula $R_6NH_2$ after which the resulting product of the general formula

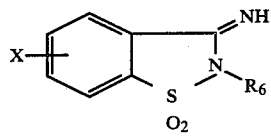

is reacted, if desired, with a substituted or non-substituted phenylisocyanate, in which a product is obtained in which $R_7$ is a substituted or non-substituted phenylcarbamoyl group; a halogen atom, an alkyl group having 1-4 carbon atoms, and an alkoxy group having 1-4 carbon atoms may be mentioned as suitable substituents for the phenylcarbamoyl group. The reaction with the amine is preferably carried out in a polar organic solvent, for example, an ether (for example, diethyl ether or dioxane), an alcohol (for example, ethyl alcohol), dimethylformamide, acetonitrile, or water (provided the acid chloride used is sufficiently resistent to hydrolysis under the reaction conditions used), or in a mixture of these solvents. The reaction is carried out at a temperature between 0° C. and the boiling point of the solvent used, preferably at a temperature between 0° C. and room temperature. The subsequent reaction with isocyanate described is preferably carried out in a polar organic solvent, for example, acetonitrile or an ether, for example, diethyl ether, at a reaction temperature between 0° C. and the boiling point of the solvent, preferably at room temperature, if desired under the influence of a base, for example, triethyl amine or sodium hydride.

The invention will now be described in greater detail with reference to the following specific examples.

EXAMPLE I

Preparation of
2-cyano-3-fluoro-N-isopropylbenzenesulphonamide

To a solution of 5.2 ml of isopropylamine in 50 ml of diethyl ether cooled in an ice bath, a solution of 4.4 g of 2-cyano-3-fluorobenzenesulphonylchloride in 50 ml of diethylether was added dropwise while stirring; reaction temperature approx. 5° C. After leaving to stand at room temperature for one hour, the reaction mixture was washed twice with ice water, dried on anhydrous $Na_2SO_4$, filtered and evaporated to dryness. The desired product was obtained in a yield of 4.16 g; melting-point 97°-105° C.

The following compounds were prepared in a corresponding manner in which, if desired, ethanol or water was used as a solvent:

2-cyano-3-chlorobenzenesulphonamide, m.p. 184°-189° C.;

2-cyano-3-chloro-N-isopropylbenzenesulphonamide, m.p. 78°-82° C.;

2-cyano-3-fluorobenzenesulphonamide, m.p. 163° C.;

2-cyano-3-chloro-N,N-diallylbenzenesulphonamide, m.p. 60° C.;

2-cyano-3-fluoro-N,N-diallylbenzenesulphonamide, m.p. 76°-78° C.;

2-cyano-3-fluoro-N,N-dimethylbenzenesulphonamide, m.p. 86°-89° C.;

2-cyano-3-fluoro-N-(3-methyl-1-butyn-3-yl)benzenesulphonamide, m.p. 118.5°-120° C.;

1-(2-cyano-3-fluorophenyl)sulphonylpiperidine, m.p. 99°-101° C.;

1-(2-cyano-3-fluorophenyl)sulphonylmorpholine, m.p. 136.5°-138° C.;

2-cyano-3-methyl-N,N-dimethylbenzenesulphonamide, m.p. 74°-77° C.;

2-cyano-3-methyl-N,N-diallylbenzenesulphonamide, m.p. 70°-72° C.;

2-cyano-3-fluoro-N,N-diethylbenzenesulphonamide, m.p. 85°-88° C.;

1-(2-cyano-3-fluorophenyl)sulphonylpyrrolidine, m.p. 96° C.;

2-cyano-5-trifluoromethoxy-N,N-dimethylbenzenesulphonamide, m.p. 100° C.;

2-cyano-5-chloro-N,N-dimethylbenzenesulphonamide, m.p. 97° C.;

and 2-cyano-3-chloro-N-(2-methoxyethyl)benzenesulphonamide, m.p. 98° C.

EXAMPLE II

Preparation of
2-cyano-3-fluoro-N,N-dichlorobenzenesulphonamide
and
S,S-dimethyl-N-(2-cyano-3-fluorophenylsulphonyl)sulphoximide.

(a) 7.55 g of 2-cyano-3-fluorobenzenesulphonamide, prepared according to Example I, was added at room temperature to 90 ml of a 10% aqueous solution of NaOCl; the temperature rose from 22° C. to 24° C. After stirring at room temperature during 1½ hour the reaction mixture was cooled in an ice bath and 16 ml of 96% acetic acid was added at approx. 10° C. After 10 minutes the solid was sucked off, washed three times with water and dried in vacuo over $P_2O_5$. 2-Cyano-3-fluoro-N,N-dichlorobenzenesulphonamide was obtained in a yield of 6.15 g; m.p. 149°-152° C.

(b) 5.4 g of 2-cyano-3-fluoro-N,N-dichlorobenzenesulphonamide was added in portions to 45 ml of 2 N sodiumhydroxide at 80° C. while stirring; the temperature rose to 90° C. After filtering the filtrate was cooled in a bath containing a mixture of ice and methanol to −10° C. The 2-cyano-3-fluoro-N-chloro-N-sodiumbenzenesulphonamide obtained was sucked off, washed successively twice with a cold saturated NaCl solution and three times with isopropanol, and dried; yield 1.06 g. 1.0 g of 2-cyano-3-fluoro-N-chloro-N-sodiumbenzenesulphonamide was added to a suspension of 0.1 g $CuCl_2$ in 5 ml of dimethyl sulphoxide. After stirring at room temperature during 1 hour and subsequently heating on a steam bath during 1 hour the reaction mixture was poured into a mixture of 30 ml water and 4 ml of a saturated solution of EDTA-$Na_2.2H_2O$ in water. After stirring for a short moment the solid was sucked off, washed three times with water and dried in vacuo over $P_2O_5$, to yield 0,50 g of S,S-dimethyl-N-(2- cyano-3-fluorophenylsulphonyl)sulphoximide; m.p. 184° C.

EXAMPLE III

Preparation of
3-amino-4-chloro-benzo[d]isothiazole-1,1-dioxide.

12.5 ml of 25% ammonia were added at approx. 60° C. to a solution of 11,8 g of 2-cyano-3-chlorobenzenesulphonylchloride in 20 ml of dioxane. After heating on a steam bath for 30 minutes the reaction mixture was cooled and diluted with water. The resulting crystalline product was sucked off, washed with water and dried. The desired product was obtained in a yield of 8.9 g. After recrystallization from ethanol, the product melted at 261°–263° C.

The following compounds were prepared in a corresponding manner:
3-amino-4-fluorobenzo[d]isothiazole-1,1-dioxide, m.p. >260° C.;
3-amino-4-methylbenzo[d]isothiazole-1,1-dioxide, m.p. 265° C.;
3-amino-4-methoxybenzo[d]isothiazole-1,1-dioxide, m.p. 270° C.;
and 3-amino-4-phenoxybenzo[d]isothiazole-1,1-dioxide, m.p. 216° C.

The same products could also be prepared by leading gaseous ammonia through a solution of the sulphonyl chloride in dioxane, or by combining the sulphonyl chloride and ammonia in ice water and then causing it to react at room temperature.
3-Amino-4-methoxybenzo[d]isothiazole-1,1-dioxide and 3-amino-4-phenoxybenzo[d]isothiazole-1,1-dioxide
could also be prepared by reacting 3-amino-4-fluorobenzo[d]isothiazole-1,1-dioxide with methanol and phenol respectively under the influence of a suitable base, e.g. a sodiumalkoxide or sodiumphenoxide, in an inert organic solvent, viz. acetonitrile, under reflux.

EXAMPLE IV

Preparation of
3-n-butylamino-4-chlorobenzo[d]isothiazole-1,1-dioxide.

A solution of 2.17 g of the 3-amino-4-chlorobenzo[d]isothiazole-1,1-dioxide prepared according to Example II and 2 ml of n-butylamine in 15 ml of dioxane was boiled for approx. 2 hours, ammonia escaping. After distilling off the solvent, the residue was stirred with water, sucked off, washed successively with water and petroleum ether and dried. The desired product was obtained in a yield of 2.4 g, melting-point 136°–138° C.

In a corresponding manner the following compounds were prepared:
3-(2-chloroethyl)amino-4-chlorobenzo[d]isothiazole-1,1-dioxide m.p. 184°–185° C.; and
3-(1-hydroxybutyl-2)amino-4-chlorobenzo[d]isothiazole-1,1-dioxide, m.p. 149° C.

EXAMPLE V

Preparation of
3-(3-cyclohexylureido)-4-chlorobenzo[d]isothiazole-1,1-dioxide.

A solution of 2.17 g of the 3-amino-4-chlorobenzo[d]isothiazole-1,1-dioxide prepared according to Example II, 1.3 g of cyclohexylisocyanate and 0.3 ml of triethylamine in 20 ml of acetonitrile was refluxed for 4 hours. After cooling the bright solution, the desired product crystallized in a yield of 2.1 g; melting-point (decomposition) 192° C.

In a corresponding manner 3-(3-methylureido)-4-chlorobenzo[d]isothiazole-1,1-dioxide was prepared; melting-point 182° C.

EXAMPLE VI

Preparation of
3-amino-4-chlorobenzo[d]isothiazole-1,1-dioxide 4.72 g of 3,4-dichlorobenzo[d]isothiazole-1,1-dioxide were added to 15 ml of 25% ammonia in 15 ml of ice water. After stirring at room temperature for two hours, the desired product was sucked off and dried; yield 4.20 g; melting-point 260° C.

In a corresponding manner 3-N',N'-dimethylhydrazino-4-chlorobenzo[d]isothiazole-1,1-dioxide, m.p. 218° C., was prepared.

EXAMPLE VII

Preparation of
2-methyl-3-imino-4-chlorobenzo[d]isothiazoline-1,1-dioxide.

7.1 g of 2-cyano-3-chlorobenzenesulphonylchloride were added to a solution of 9 ml of methylamine in approx. 15 ml of water cooled at 0° C. After stirring at 0°–10° C. for 1 hour, the solid was sucked off, washed with water and dried in air. The desired product was obtained in a yield of 5,5 g; melting-point 140°–142° C.

In a corresponding manner the following compounds were prepared:
2-allyl-3-imino-4-chlorobenzo[d]isothiazoline-1,1-dioxide, m.p. 92,5°–95° C.;
2-methyl-3-imino-4-fluorobenzo[d]isothiazoline-1,1-dioxide, m.p. 142° C.;
2-allyl-3-imino-4-fluorobenzo[d]isothiazoline-1,1-dioxide, m.p. 101° C.;
2-methyl-3-imino-4-methoxybenzo[d]isothiazoline-1,1-dioxide, m.p. 138° C.;
and 2-ethyl-3-imino-4-fluorobenzo[d]isothiazoline-1,1-dioxide, m.p. 110° C.

EXAMPLE VIII

Preparation of
2-methyl-3-N-(4-ethoxyphenylcarbamoyl)imino-4-chlorobenzo[d]isothiazoline-1,1-dioxide.

2.3 g of 2-methyl-3-imino-4-chlorobenzo[d]isothiazoline-1,1-dioxide were dissolved in 15 ml of acetonitrile, 1.6 ml of 4-ethoxyphenylisocyanate were added to this bright solution, after which the reaction mixture was left to stand overnight at room temperature. After evaporating the solvent under reduced pressure at 30° C., the residue was suspended in ether. After sucking off, the desired product was obtained in a yield of 1.0 g; melting-point 147°–154° C.

EXAMPLE IX

The compounds according to the invention were processed to compositions by suspending the compounds in water in the presence of a dispersing agent, such as lignine sulphonate, and/or a wetting agent, such as alkylnaphthalene sulphonate, an alkyl sulphate, an alkylbenzenesulphonate, an alkylpolyoxyethylene or an alkylarylpolyoxyethylene. A typical formulation comprises 25% by weight of active substance, 2% by weight of an alkyl naphthalene sulphonate, 5% by weight of a lignine sulphonate, and 68% by weight of kaolin. Young broad bean plants, approx. 10 cm high, were headed on two pair of leaves and then sprayed with the composition thus obtained in various concentrations. After the plants had dried up, they were infected with *Aphis fabae* (black bean aphids) by placing 10 aphids on each plant. The plants were then stored in a climate cell at a temperature of 20°/15° C., a light-dark cycle of 18/6 hours being maintained; relative humidity 65/70%. After 7 days the mortality of the aphids was established. Each experiment was carried out in quadruplicate. The results are recorded in the Table A below. The meanings of the symbols recorded in the table are as follows:

+ = 90–100% mortality
± = 50–90% mortality
− = <50% mortality.

TABLE A

| compound no. | Activity against *Aphis fabae* conc. in mg active substance per liter | | | | | |
|---|---|---|---|---|---|---|
| | 300 | 100 | 30 | 10 | 3 | 1 |
| blank | − | | | | | |
| (1) | + | + | + | + | ± | − |
| (2) | + | + | + | ± | − | |
| (3) | + | + | + | − | | |
| (4) | + | + | + | ± | − | |
| (5) | + | + | + | ± | − | |
| (6) | + | + | + | ± | − | |
| (7) | + | + | + | ± | − | |
| (8) | + | + | + | ± | − | |
| (9) | ± | ± | ± | ± | − | |
| (10) | ± | ± | ± | ± | − | |
| (11) | + | + | ± | ± | − | |
| (12) | + | + | + | − | | |
| (13) | + | + | + | ± | − | |
| (14) | + | + | − | | | |
| (15) | + | + | ± | − | | |
| (16) | + | + | ± | − | | |
| (17) | + | ± | ± | − | | |
| (18) | + | + | ± | − | | |
| (19) | ± | ± | ± | − | | |
| (20) | + | + | ± | − | | |
| (21) | + | + | ± | − | | |
| (22) | + | + | ± | − | | |
| (23) | + | ± | ± | − | | |
| (24) | + | + | − | | | |
| (25) | + | + | + | | | |
| (26) | + | + | − | | | |
| (27) | + | + | ± | − | | |
| (28) | + | | | | | |
| (29) | + | | | | | |
| (30) | + | | | | | |
| (31) | + | + | − | | | |
| (32) | + | + | ± | − | | |
| (33) | + | | | | | |
| (34) | + | | | | | |
| (35) | + | | | | | |
| (36) | + | + | ± | − | | |
| (37) | + | | | | | |

EXAMPLE X

Young broad bean plants of 15–20 cm high in plastic pots of approx. 12 cm diameter were headed on 3 fully developed leaves. The plants were then infected with *Aphis fabae* by placing pieces of broad bean plants fully infected with *Aphis fabae* on the leaves of the test plants. The aphids then move from the wilting infection material to the fresh test plants. After 24 hours, first the wilted stems were removed, after which the test plants were sprayed from below and from the top with the compositions obtained according to Example IX in various concentrations. After 6 days in the glasshouse at 20°–24° C. the mortality of the aphids was established. Three broad bean plants were used for each test. The average results are recorded in Table B below, in which the mortality percentage shown in corrected for the mortality of the aphids on untreated broad bean plants.

TABLE B

| compound no. | Activity against *Aphis fabae* (% mortality) conc. in mg of act. substance per liter | | | | |
|---|---|---|---|---|---|
| | 100 | 30 | 10 | 3 | 1 |
| (1) | 100 | 97 | 47 | | |
| (5) | | 100 | 91 | 13 | 0 |
| (6) | | 100 | 92 | 13 | |
| (7) | 100 | 85 | 10 | | |
| (10) | | 98 | 48 | 4 | |
| (11) | | 100 | 84 | 10 | |
| (16) | 86 | 32 | 0 | | |
| (17) | 93 | 16 | 0 | | |
| (18) | 96 | 27 | 0 | | |
| (19) | | 100 | 78 | 2 | |
| (21) | 100 | 65 | 10 | | |

EXAMPLE XI

Young broad bean plants, 15–20 cm high in plastic pots of approx. 12 cm diameter were headed and then infected as described in Example X. After the infection the plants were sprayed with a composition obtained according to Example VIII which contained 3-amino-4-chlorobenzo[d]isothiazole-1,1-dioxide (comp. No. 1) in various concentrations (three plants per concentration). The pots were placed in the open air and the mortality of the aphids was established after 3 and 7 days. The results are recorded in Table C, in which the mortality percentage is corrected for the mortality of aphids on untreated broad bean plants.

TABLE C

| Number of days after spraying | Activity against *Aphis fabae* (% mortality) conc. in mg of act. substance per liter | | | |
|---|---|---|---|---|
| | 100 | 30 | 10 | 3 |
| 3 | 95 | 0 | 0 | 0 |
| 7 | 100 | 95 | 70 | 0 |

EXAMPLE XII

The systemic activity of 3-amino-4-chlorobenzo[d]isothiazole-1,1-dioxide (compound no. 1) was determined as follows. Young broad bean plants of 15–20 cm high, placed in pots of approx. 12 cm diameter (soil area per pot approx. 100 cm$^2$), were treated in the glasshouse as follows. The soil in each pot was watered with 50 ml of water, to which a given quantity of the compound to be tested had been added. After infecting the plants as described in Example X, in which, however, the heading operation of the plants was omitted, the aphicidal activity of the active substance absorbed via the roots was established by evaluating the mortality percentage of the aphids 6 days after the infection: Table D (the results are corrected for the mortality on the untreated plants). As appears from Table D. an interesting residual activity was found when the infection was delayed to 5 and 7 weeks, respectively, after the treatment with the aphicidal composition.

TABLE D

| Activity against *Aphis fabae* (% mortality) | | | | |
|---|---|---|---|---|
| Number of weeks between | dosage in mg of act. subst. per liter | | | |
| treatment and infection | 10 | 3 | 1 | 0.3 |
| 0 | 100 | 96 | 80 | 20 |
| 5 | 99 | 82 | | |
| 7 | 92 | 20 | | |

The found systemic activity was deemed of great importance by those skilled in the art.

EXAMPLE XIII

3-Amino-4-chlorobenzo[d]isothiazole-1,1-dioxide (comp. no. 1) was tested in small field trials against *Aphis fabae* on broad beans by bringing the compositions in the top layer of the soil; the active substance was used in the form of a suspension as described in Example IX. Six days after the infection the plants were evaluated, in which the corrected mortality percentages recorded in Table E were obtained (results are corrected for the mortality on the untreated plants). As appears from the Table, the infection could be delayed without objection to at least 7 weeks after the treatment.

TABLE E

| Activity against *Aphis fabae* (% mortality) | | | | | | | | |
|---|---|---|---|---|---|---|---|---|
| Dosage in mg of act. substance per 0.25 m² | Number of weeks between treatm. and inf. | | | | | | | |
|  | 0 | 1 | 2 | 3 | 4 | 5 | 6 | 7 |
| 2000 | 90 | 98 | 100 | 98 | 100 | 100 | 100 | 100 |
| 1000 | 87 | 90 | 100 | 90 | 100 | 96 | 93 | 100 |
| 500 | 90 | 90 | 100 | 100 | 100 | 97 | 99 | 99 |

EXAMPLE XIV

The effect of the addition of mineral oils like the aliphatic hydrocarbon Sunoil 7 N (a) and the naphthenic hydrocarbon Sunoil 91 N (b), of a vegetable oil like a cotton seed oil (c), of a glycolether like trioxitol (d), of an alkylbenzene like Dobane (e), of a polyoxyethylene sorbitan ester, like the polyoxyethylene sorbitan mono-oleate Tween 80 (f), the polyoxyethylene sorbitan monolaurate Tween 21 (v) and the polyoxyethylene sorbitan monolaurate Tween 22 (w), of a fatty acid polyglycolester like Emulsogen EL (g), of alkylated phenol polyoxyethylene compounds like the isooctylphenol polyoxyethylene Citowett (h), the nonylphenyl polyoxyethylene Agral LN (i), Arkopal N 060 (j), Arkopal N 090 (k), Arkopal N 130 (l) and Arkopal N 150 (m), the tributylphenol polyoxyethylene Sapogenat T 060 (n) and Sapogenat T 180 (o), of a polyoxyethylene alkyl ether like the polyoxyethylene laurylether Brij 30 (p), of a polyethylglycol compound like Carbowax 600 (q), of ureum (r), of a quaternary ammonium compound like Aliquat 221 (s), of a mixture of a mineral oil and surfactant like Atplus 411 F (t), and of a polymeric resin with coupling agents like Atplus 536 (u), on the aphicidal activity of 3-amino-4-chlorobenzo[d]isothiazole-1,1-dioxide (comp. no. 1) was tested according to the method described in Example X. The results recorded in Table F (% mortality) were obtained when 1 (6) days after the treatment the plants were evaluated.

TABLE F

| | | Aphicidal activity (% mortality) | | | |
|---|---|---|---|---|---|
| | | Conc. in mg of act. subst. per liter | | | |
| additive | mg/l | 30 | 10 | 3 | 1 |
| None | — | 21(92) | 11(43) | 0(7) | — |
| (a) | 5000 | 47(100) | 40(100) | 5(98) | — |
| (a) | 2500 | 43(100) | 27(100) | 17(95) | 8(77) |
| (b) | 500 | — | 3(96) | 0(67) | 0(20) |
| (c) | 500 | — | 23(98) | 0(60) | 0(20) |
| (d) | 5000 | 37(99) | 17(97) | 2(62) | — |
| (e) | 2500 | 88(100) | 80(99) | 63(98) | — |
| (f) | 500 | — | 43(100) | 7(33) | — |
| (g) | 500 | — | 27(100) | 3(10) | — |
| (h) | 500 | — | 73(98) | 13(47) | 0(7) |
| (i) | 500 | — | 57(99) | 3(37) | — |
| (i) | 1000 | — | 70(99) | 20(50) | — |
| (j) | 500 | — | 96(100) | 30(90) | 0(23) |
| (k) | 500 | — | 93(100) | 2(87) | 0(17) |
| (l) | 500 | — | 80(100) | 3(90) | 0(7) |
| (m) | 500 | — | 75(100) | 0(90) | — |
| (n) | 500 | — | 98(100) | 43(80) | 3(7) |
| (o) | 500 | — | 92(100) | 33(82) | 0(7) |
| (p) | 500 | — | 87(100) | 57(63) | 20(20) |
| (q) | 500 | — | 0(96) | 0(13) | — |
| (r) | 500 | — | 3(67) | — | — |
| (s) | 500 | — | 90(99) | 33(47) | — |
| (t) | 500 | — | 80(99) | 27(77) | 0(20) |
| (u) | 500 | — | 90(96) | 20(27) | — |
| (v) | 500 | — | 47(99) | 10(27) | — |
| (w) | 500 | — | 33(100) | 0(27) | — |

In the absence of the tested aphicidal compound, the following additives as such, namely 5000 ppm Sunoil 7 N, 2500 ppm Sunoil 7 N, 5000 ppm Trioxitol, 2500 ppm Dobane, and 500 ppm Arkopal N090, gave 5(23), 0(7), 0(0), 0(0) and 0(0)% mortality, respectively, upon evaluation after 1(6) days.

EXAMPLE XV

The effect of smaller additions of Sunoil 7 N on the aphicidal activity against *Aphis fabae* of 3-amino-4-chlorobenzo[d]isothiazole-1,1-dioxide (comp. no. 1) was tested according to the method described in Example XI. The results recorded in table G (% mortality) were obtained when the plants were evaluated 6 days after the treatment.

TABLE G

| | Aphicidal activity (% mortality) | | | |
|---|---|---|---|---|
| | Conc. in mg of act. substance per liter | | | |
| Additive in mg/l | 30 | 10 | 3 | 1 |
| None | 100 | 94 | 23 | |
| Sunoil 7 N, 2500 | 100 | 100 | 100 | 90 |
| Sunoil 7 N, 500 | 100 | 100 | 94 | 37 |
| Sunoil 7 N, 100 | 100 | 99 | 93 | 57 |

EXAMPLE XVI

Young potato plants, approx. 15 cm high, were infected with *Myzus persicae* in the same way as described in Example X for the infection with *Aphis fabae*. After infection the test plants were sprayed from below and from the top with a composition obtained according to Example IX in various concentrations (three plants per concentration), which composition comprised 3-amino-4-chlorobenzo[d]isothiazole-1,1-dioxide (comp. no. 1) as the active substance. After 6 days in the glasshouse at 20°-24° C. the mortality of the aphids was determined. The average results are presented in table H below, in which the mortality percentage shown is corrected for the mortality of the untreated potato plants.

The effect of several additives on the aphicidal activity of the above active substance was also tested. The results are presented in table H. The letters used for the additives in table H correspond to the letters used in Example XIV.

TABLE H

| Aphicidal activity against Myzus persicae (% mortality) | | | | |
|---|---|---|---|---|
| | | Conc. in mg active subst. per liter | | |
| additive | mg/l | 30 | 10 | 3 |
| none | — | 95 | 70 | — |
| (k) | 500 | 100 | 97 | 40 |
| (l) | 500 | 100 | 99 | 40 |
| (i) | 1000 | 100 | 99 | 43 |
| (h) | 500 | 100 | 100 | 67 |
| (p) | 500 | 100 | 100 | 80 |

EXAMPLE XVII

In the same way as described in Example XI the aphicidal activity of 3-amino-4-chlorobenzo[d]isothiazole-1,1-dioxide (compound no. 1) against *Aphis fabae* was investigated; the tests were carried out on broad bean plants in the open air as described in Example XI. The effect of several additives (see Examples XIV and XVI) was determined. The results presented in table K were obtained when 6 days after the treatment the plants were examined to determine the mortality of the aphids. The letters used for the additives in table K correspond to the letters used in Example XIV.

TABLE K

| Activity; % mortality after 6 days | | | | |
|---|---|---|---|---|
| | | Conc. in mg act. per liter | | |
| additive | mg/l | 30 | 10 | 3 |
| none | — | 100 | 99 | 63 |
| (p) | 250 | | 100 | 91 |
| (m) | 250 | | 100 | 83 |
| (h) | 250 | | 100 | 89 |
| (a) | 250 | | 100 | 97 |

EXAMPLE XVIII

The aphicidal activity of 3-amino-4-chlorobenzo[d]isothiazole-1,1-dioxide (compound no. 1) against *Aphis fabae* was tested in several formulations in the same way as described in Example X.

The formulations were prepared according to known formulation techniques as described in the specification. The formulations used are defined as follows: Suspension A comprises 7 parts by wt. of a lignine sulphonate, 3 parts by wt. of an alkylnaphthalene sulphonate and 30 parts by wt. of active substance, diluted with water up to the desired concentration.

Liquid B comprises 10% by wt. of active substance, 20% by wt. of an alkylphenolpolyoxyethylene, and 70% by wt. of dimethylformamide. Liquid C comprises 10% by wt. of active substance, 20% by wt. of an alkylphenolpolyoxyethylene, and 70% by wt. of N-methylpyrrolidone. Wettable powder D comprises 25% by wt. of active substance, 2% by wt. of an alkylnaphthalene sulphonate, 5% by wt. of a lignine sulphonate, and 68% by wt. of kaolin. After 6 days in the glasshouse the mortality of the aphids was determined. The results are presented in table L below.

TABLE L

| Aphicidal activity; % Mortality after 6 days | | | |
|---|---|---|---|
| | Conc. in mg active per liter | | |
| formulation | 30 | 10 | 3 |
| suspension A | 97 | 47 | 7 |
| liquid B | 100 | 97 | 0 |
| liquid C | 100 | 96 | 17 |
| wettable powder D | 97 | 67 | 17 |

EXAMPLE XIX

The aphicidal activity of 3-amino-4-chlorobenzo[d]isothiazole-1,1-dioxide (compound no. 1) against *Aphis fabae* was tested in some formulations in the open air in the same way as described in Example XI.

The formulations used are defined as follows: Wettable powder F comprises 25% by wt. of active substance, 2% by wt. of an alkylnaphthalene sulphonate, 5% by wt. of a lignine sulphonate, and 68% by wt. of kaolin. Liquid G comprises 10% by wt. of active substance, 20% by wt. of an alkylphenolpolyoxyethylene, and 70% by wt. of dimethylformamide.

After 6 days in the open air the mortality of the aphids was determined. The results are presented in table M.

TABLE M

| Aphicidal activity; % mortality after 6 days | | | |
|---|---|---|---|
| | Conc. in mg active per liter | | |
| formulation | 30 | 10 | 3 |
| wettable powder F | 100 | 99 | 63 |
| liquid G | 100 | 100 | 63 |

EXAMPLE XX

The systemic activity of several formulations comprising 3-amino-4-chlorobenzo[d]isothiazole-1,1-dioxide (compound no. 1) against Aphis fabae was determined as described in Example XII by mixing the composition through the soil. 2 Weeks after the treatment of the soil the plants were infected as described in Example X. 6 Days after the infection the mortality of the aphids was determined. After each week the infection was repeated; evaluation at each time 6 days after the infection.

The formulations used are defined as follows: Suspension H comprises 1 part by wt. of a polyoxyethylenated sorbitan monooleate, 2 parts by wt. of a lignine sulphoneate and 7 parts by wt. of active substance, diluted with water up to the desired concentration. Wettable powder I comprises 25% by wt. of active substance, 2% by wt. of an alkylnaphthalene sulphonate, 5% by wt. of a lignine sulphonate, and 68% by wt. of kaolin. Granule J comprises 2.5% by wt. of active substance, 7.5% by wt. of kaolin, 6.7% by wt. of a lignine sulphonate, and 83.3% by wt. of a granular silicate. Granule K comprises 2.5% by wt. of active substance, 7.5% by wt. of kaolin, 5% by wt. of polyvinylacetate, and 85% by wt. of a granular silicate. Granule L comprises 2.5% by wt. of active substance, 7.5% by wt. of kaolin, 5% by wt. of sodium-silicate and 85% by wt. of a granular silicate. The results are presented in table N.

TABLE N

Aphicidal activity; % mortality at (re)-infection in ... weeks after treatment of the soil and subsequent evaluation after 6 days.

| composition | mg act. per pot | weeks | | | | | | | | | | | |
|---|---|---|---|---|---|---|---|---|---|---|---|---|---|
| | | 2 | 3 | 4 | 5 | 6 | 7 | 8 | 9 | 10 | 11 | 12 | 13 |
| Suspension H | 1 | 100 | 100 | 100 | 100 | 100 | 100 | 98 | 85 | 63 | 33 | 0 | |
| Suspension H | 3 | 100 | 100 | 100 | 100 | 100 | 100 | 100 | 100 | 94 | 91 | 77 | 52 |
| W.P. I | 1 | 100 | 100 | 99 | 99 | 100 | 98 | 95 | 73 | 53 | 23 | 10 | |
| W.P. I | 3 | 100 | 100 | 100 | 100 | 100 | 100 | 100 | 99 | 96 | 93 | 85 | 63 |
| Granule J | 1 | 100 | 100 | 100 | 100 | 100 | 100 | 99 | 70 | 40 | 23 | 7 | |
| Granule J | 3 | 100 | 100 | 100 | 100 | 100 | 100 | 100 | 100 | 99 | 98 | 90 | 75 |
| Granule K | 1 | 100 | 100 | 100 | 99 | 99 | 99 | 97 | 80 | 67 | 37 | 7 | |
| Granule K | 3 | 100 | 100 | 100 | 100 | 100 | 100 | 100 | 99 | 96 | 93 | 83 | 50 |
| Granule L | 1 | 100 | 100 | 100 | 100 | 100 | 99 | 99 | 83 | 70 | 53 | 20 | |
| Granule L | 3 | 100 | 100 | 100 | 100 | 100 | 100 | 100 | 99 | 94 | 93 | 88 | 70 |

EXAMPLE XXI

The investigations described in Example XX were repeated in field trials. The trials were carried out on broad bean plants against Aphis fabae; active substance 3-amino-4-chlorobenzo[d]isothiazole-1,1-dioxide (compound no. 1). After each visual evaluation and before the next (re-) infection the plants were freed from aphids. The soil was treated by 10 cm deep spadeing of the composition into the soil.

The results are presented in table O. It should be remarked, that during these trials the weather conditions were very bad: it was extremely wet.

TABLE O

Aphicidal activity; % mortality at (re-)-infection in ... weeks after treatment of the soil and subsequent evaluation after 6 days.

| composition | kg active subst. per hectare | weeks | | |
|---|---|---|---|---|
| | | 1 | 3 | 5 |
| W.P. I | 10 | 99 | 100 | 83 |
| W.P. I | 3 | 99 | 63 | 10 |
| W.P. I | 1 | 27 | 27 | 0 |
| Granule J | 10 | 100 | 100 | 88 |
| Granule J | 3 | 98 | 63 | 13 |
| Granule J | 1 | 50 | 30 | 0 |

EXAMPLE XXII

Young cotton plants, approx. 10 cm high, were infected with Aphis gossypii (cotton aphid) in the same way as described in Example X for the infection with Aphis fabae. After infection the test plants were sprayed from below and from the top with a composition obtained according to Example IX in various concentrations, which composition comprised 3-amino-4-chlorobenzo[d]isothiazole-1,1-dioxide (compound no. 1) as the active substance and an additive. After 6 days in a climate room at 20° C. the mortality of the aphids was determined. The results are presented in table P. As in all further experiments the results are corrected for the mortality on the untreated plants. The letters used for the additives in table P correspond to the letters used in Example XIV.

TABLE P

Activity against *Aphis gossypii*; % mortality

| additive | mg/l | conc. in mg active per liter | | | |
|---|---|---|---|---|---|
| | | 100 | 30 | 10 | 3 |
| (h) | 250 | 100 | 100 | 100 | 100 |
| (i) | 250 | 100 | 100 | 100 | 70 |

EXAMPLE XXIII

Young broad bean plants, approx. 10 cm high, were infected with Acyrthosiphon pisum (bean aphid) in the same way as described in Example X, and subsequently treated as described in Example XXII. Active substance: 3-amino-4-chlorobenzo[d]isothiazole-1,1-dioxide (compound no. 1). After 5 days in a climate room at 20° C. the mortality of the aphids was determined. The results are presented in table Q.

TABLE Q

Activity against *Acyrthosiphon pisum*; % mortality

| additive | mg/l | conc. in mg active per liter | | |
|---|---|---|---|---|
| | | 30 | 10 | 3 |
| none | — | 28 | 20 | 8 |
| Agral LN | 250 | 97 | 74 | 60 |
| Arkopal N150 | 250 | 97 | 57 | 0 |

Agral LN and Arkopal N 150 as such in the above amounts caused 5 and 0% mortality respectively after 5 days.

EXAMPLE XXIV

Young oat plants, approx. 15 cm high, were infected with Sitobion avenae (small corn aphid) in the same way as described in Example X, and subsequently treated as described in Example XXII. Active substance: 3-amino-4-chlorobenzo[d]isothiazole-1,1-dioxide (compound no. 1).

After 6 days in a climate room at 20° C. the mortality of the aphids was determined. The results are presented in table R.

TABLE R

Activity against *Sitobion avenae*; % Mortality

| additive | mg/l | Conc. in mg active per liter | | | |
|---|---|---|---|---|---|
| | | 100 | 30 | 10 | 3 |
| Agral LN | 250 | 100 | 100 | 100 | 71 |
| Citowett | 250 | 92 | 97 | 100 | 55 |

Agral LN and Citowett as such in the above amounts caused 6 and 11% mortality respectively after 6 days.

EXAMPLE XXV

Young Brussels sprout plants, approx. 10 cm high, were infected with Brevicoryne brassicae (mealy cabbage aphid) in the same way as described in Example X, and subsequently treated as described in Example XXII. Active substance: 3-amino-4-chlorobenzo[d]isothiazole-1,1-dioxide (compound no. 1). After 6 days in a climate room at 20° C. the mortality of the aphids was determined. The results are presented in table S.

TABLE S

| | | Activity against *Brevicoryne brassicae*; % mortality after 6 days | | | | |
|---|---|---|---|---|---|---|
| | | conc. in mg active per liter | | | | |
| additive | mg/l | 100 | 30 | 10 | 3 | 1 |
| Citowett | 250 | 92 | 58 | 39 | 23 | 5 |

EXAMPLE XXVI

Young potato plants, approx. 15 cm high, were infected with Myzus persicae in the same way as described in Example XVI. The aphicidal activity was determined in the open air as described in Example X. Active compound: 3-amino-4-chlorobenzo[d]isothiazole-1,1-dioxide (compound No. 1). The effect of several additives, specified in previous Examples, was tested. The results, presented in Table T, were obtained when 6 days after the treatment the plants were examined to determine the mortality of the aphids. The letters used for the additives in table T correspond to the letters used in Example XIV.

TABLE T

| | | Activity against *Myzus persicae*; % mortality after 6 days | | |
|---|---|---|---|---|
| | | conc. in mg active per liter | | |
| additive | mg/l | 30 | 10 | 3 |
| none | — | 96 | 92 | 53 |
| (p) | 250 | — | 98 | 85 |
| (m) | 250 | — | 99 | 63 |
| (h) | 250 | — | 96 | 87 |
| (a) | 250 | — | 99 | 60 |

We claim:
1. Compounds of the general formula

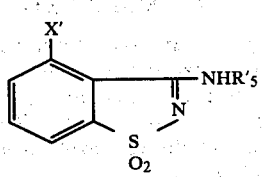

wherein
X' is a fluorine atom or a chlorine atom, and
R5' is a hydrogen atom, a 2-chloroethyl group, or a cyclohexylcarbamoyl group.

2. Compounds of the general formula

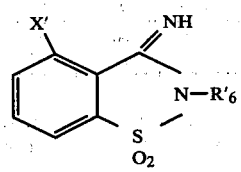

wherein
X' is a fluorine atom or a chlorine atom, and
R6' is a methyl group or ethyl group.

3. 3-Amino-4-chlorobenzo[d]isothiazole-1,1-dioxide.
4. 3-(3-Cyclohexylureido)-4-chlorobenzo[d]isothiazole-1,1-dioxide.
5. 3-(2-chloroethyl)amino-4-chlorobenzo[d]-isothiazole-1,1-dioxide.
6. 2-Ethyl-3-imino-4-fluorobenzo[d]isothiazoline-1,1-dioxide.
7. An aphicidal composition, characterized in that, in addition to a solid or liquid inert carrier meterial, the composition comprises a compound of the general formula

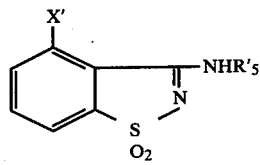

where
X' is a fluorine atom or a chlorine atom, and
R5' is a hydrogen atom, a 3-chloroethyl group, or a cyclohexylcarbamoyl group.

8. A composition as claimed in claim 7, characterized in that the composition comprises in addition one or more of the following additives: an aliphatic or naphthenic mineral oil, a vegetable oil, a glycol ether, an alkylated benzene, a polyoxyethylene compound, urea, a polymeric resin compound, and a surfactant such as a polyoxyethylene sorbitan ester, a fatty acid polyglycol ester, an alkylated phenol polyoxyethylene, a polyoxyethylene alkyl ether or a quaternary ammonium compound; and, if desired, a phytotoxicity-reducing substance.

9. A composition as claimed in claim 7 or 8, characterized in that the active constituent is a compound of the general formula

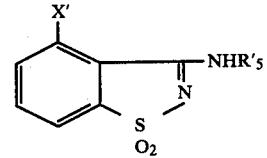

wherein X' and R5' have the meanings given in claim 3.

10. A composition as claimed in claim 7 or 8, characterized in that the active constituent is a compound of the general formula

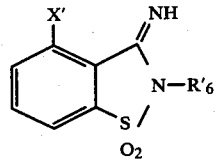

wherein X' and R6' have the meanings given in claim 4.

11. A composition as claimed in claim 7 or 8, characterized in that the active constituent is 3-amino-4-chlorobenzo[d]isothiazole-1,1-dioxide.

12. A composition as claimed in claim 7 or 8, characterized in that the active constituent is 3-(3-cyclohexylureido)-4-chlorobenzo[d]isothiazole-1,1-dioxide.

13. A composition as claimed in claim 7 or 8, characterized in that the active constituent is 3-(2-chloroethyl)amino-4-chlorobenzo[d]isothiazole-1,1-dioxide.

14. A composition as claimed in claim 7 or 8, characterized in that the active constituent is 2-ethyl-3-imino-4-fluorobenzo[d]isothiazoline-1,1-dioxide.

* * * * *